(12) United States Patent
Kimura et al.

(10) Patent No.: US 8,771,676 B2
(45) Date of Patent: Jul. 8, 2014

(54) AGROCHEMICALLY ACTIVE MICROBIAL FORMULATION

(75) Inventors: Shinya Kimura, Toyonaka (JP); Yoshiki Takashima, Nishinomiya (JP); Takeshi Maruyama, Kobe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1712 days.

(21) Appl. No.: 11/767,095

(22) Filed: Jun. 22, 2007

(65) Prior Publication Data

US 2009/0035280 A1 Feb. 5, 2009

(30) Foreign Application Priority Data

Jun. 23, 2006 (JP) .............................. 2006-173686
Jun. 23, 2006 (JP) .............................. 2006-173687
Jun. 23, 2006 (JP) .............................. 2006-173688
Oct. 27, 2006 (JP) .............................. 2006-292106
Nov. 29, 2006 (JP) .............................. 2006-321454

(51) Int. Cl.
*A61K 38/00* (2006.01)

(52) U.S. Cl.
USPC ...... 424/93.5; 424/93.1; 435/243; 435/252.1; 435/254.1; 435/255.2; 560/1

(58) Field of Classification Search
USPC ........ 435/252.1, 254.1, 255.1, 243; 424/93.5, 424/93.1; 560/1
See application file for complete search history.

(56) References Cited

U.S. PATENT DOCUMENTS 4,829,101 A * 5/1989 Kraemer et al. .............. 523/201
6,103,248 A * 8/2000 Burkhart et al. .............. 424/401
7,033,586 B2 * 4/2006 Shimizu et al. .............. 424/93.5
2003/0077225 A1 * 4/2003 Laurent et al. .................. 424/9.3
2004/0116541 A1 * 6/2004 Calderon et al. ................. 516/54
2007/0141032 A1 * 6/2007 Matsumura et al. .......... 424/93.5
2007/0244153 A1 * 10/2007 Kakimoto et al. ............. 514/311

FOREIGN PATENT DOCUMENTS

| JP | 57158703 A | * | 9/1982 |
| JP | 2004217637 A | * | 8/2004 |
| JP | 2005013849 A | * | 1/2005 |
| JP | 45014262 B | * | 4/2010 |

OTHER PUBLICATIONS

Chemical Book data sheet for triolein; http://www.chemicalbook.com/ProductChemicalPropertiesCB2715065_EN.htm, downloaded Aug. 13, 2010, 3 pages.*
Lehninger, A. "Biochemistry" (1975) (Worth Publishers, Inc.: New York, NY), p. 281.*
English translation of JP 2004217637 downloaded from JPO Aug. 14, 2010.*
English translation of JP 4501426 downloaded from JPO Aug. 14, 2010.*
Fordyce et al. J. Am. Chem. Soc. (1933) 55(8): 3368-3372.*
STN abstract for JP57158703 downloaded from CAPLUS Aug. 13, 2010.*
STN abstract for JP2005013849 downloaded from CAPLUS Aug. 13, 2010.*
English translation for JP2005013849. Downloaded from the JPO on Aug. 25, 2010.*
English translation for JP 57158703.*

* cited by examiner

*Primary Examiner* — Susan Hanley
(74) *Attorney, Agent, or Firm* — Sughrue Mion, PLLC

(57) ABSTRACT

The present invention provides an agrochemically active microbial formulation comprising a combination of an agrochemically active microbe with a specified ester compound and a surfactant, the formulation exhibiting a stable pest controlling effect with no harmful effect on a plant and having highly stable viability of the agrochemically active microbe.

39 Claims, No Drawings

AGROCHEMICALLY ACTIVE MICROBIAL FORMULATION

BACKGROUND OF THE INVENTION

1. Field of the Invention

The present invention relates to an agrochemically active microbial formulation and the like.

2. Background of the Invention

As a method for controlling insect pests avoiding use of a chemically synthesized compound as an active ingredient, the use of an agrochemically active microbe has drawn an attention, and there have been known agrochemically active microbial formulations comprising an agrochemically active microbe (specifically, for example, pest controlling filamentous fungus) is known (for example, see U.S. Pat. Nos. 5,730, 973, 6,030,924). As a method for increasing the pest control effect of such agrochemically active microbial formulations, for example, applying a mixture of an agrochemically active microbe (specifically, for example, pest controlling filamentous fungus) and an oil such as a vegetable oil and a mineral oil is known (for example, see WO 95/10597, J. Invert. Pathol. 52, 66-72 (1988), Ann. Appl. Biol. 122, 145-152 (1993), Pestic. Sci. 46, 299-306 (1996), Phytoparasitica 25, 93S-100S (1997), Japanese Journal of Applied Entomology and Zoology 44 4, 241-243 (2000), and Biocontrol Science and Technology 12, 337-348 (2002)).

However, some agrochemically active microbes (particularly, pest controlling filamentous fungus) alone exhibit not high-stable viability. When an agrochemically active microbial formulation comprising such an agrochemically active microbe is used by applying a mixture of the agrochemically active microbe and an oil such as a vegetable oil and a mineral oil, it is not necessarily easy to select a combination of components and a combination ratio thereof. Further, since the formulation is prepared giving higher priority to stability of viability of the agrochemically active microbe (particularly pest controlling filamentous fungus), the formulation is sometimes not emulsified well, resulting in a heterogeneous mixture, thereby the pest controlling effect is not stabilized, and the formulation may have harmful effects on plants (for example, see Year Heisei 12 Seibutsu-Nouyaku-Renraku-Shiken-Seiseki edited by Japan Plant Protection Association 93 (2000), and Year Heisei 13 Seibutsu-Nouyaku-Renraku-Shiken-Seiseki edited by Japan Plant Protection Association 198 (2001)).

SUMMARY OF THE INVENTION

The present invention provides an agrochemically active microbial formulation comprising a combination of an agrochemically active microbe with a specified ester compound and a surfactant. The formulation exhibits a stable pest controlling effect with no harmful effect on a plant, and has highly stable viability of the agrochemically active microbe.

That is, the present invention provides:
1) An agrochemically active microbial formulation (hereinafter, referred to as a present formulation in some cases), comprising at least one kind of ester compound (hereinafter, referred to as a present ester compound in some cases), a surfactant suitable for emulsifying the ester compound (hereinafter, referred to as a present surfactant) and an agrochemically active microbe, wherein the ester compound is selected from the following group:
    (1) an ester compound which is liquid at 25° C., of monovalent fatty acid and polyhydric alcohol represented by the formula (I):

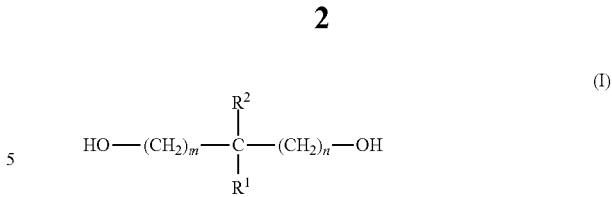

wherein $R^1$ and $R^2$ are the same or different, and represent a hydrogen atom, a methyl group, an ethyl group, a hydroxymethyl group or a 2-hydroxyethyl group, and m and n are the same or different, and represent 1 or 2, provided that $R^1$ and $R^2$ are not a hydrogen atom at the same time;
    (2) an ester compound which is liquid at 25° C., of diglycerin and monovalent fatty acid; and
    (3) a diester compound which is liquid at 25° C., of adipic acid and monohydric alcohol;
2) An agrochemically active microbial formulation according to the item 1, wherein the polyhydric alcohol represented by the formula (I) is pentaerythritol, trimethylolalkane or neopentyl glycol;
3) The agrochemically active microbial formulation according to the item 1 or 2, wherein the monovalent fatty acid is 2-ethylhexanoic acid, isomer of n-octadecanoic acid, or capric acid;
4) The agrochemically active microbial formulation according to the item 1, 2 or 3, wherein the monohydric alcohol is 2-heptylundecyl alcohol;
5) The agrochemically active microbial formulation according to the item 1, wherein the ester compound is at least one kind of ester compound selected from:
    (a) a tetraester compound which is liquid at 25° C., of pentaerythritol and 2-ethylhexanoic acid,
    (b) a triester compound which is liquid at 25° C., of trimethylolpropane and isomer of n-octadecane,
    (c) a diester compound which is liquid at 25° C., of neopentyl glycol and capric acid,
    (d) a tetraester compound which is liquid at 25° C., of diglycerin and isomer of n-octadecanoic acid,
    (e) a triester compound which is liquid at 25° C., of diglycerin and isomer of n-octadecanoic acid, and
    (f) a diester compound which is liquid at 25° C., of adipic acid and 2-heptylundecyl alcohol;
6) The agrochemically active microbial formulation according to any one of the items 1 to 5, wherein the surfactant is a nonionic surfactant;
7) The agrochemically active microbial formulation according to any one of the items 1 to 5, wherein the surfactant is at least one kind of nonionic surfactant selected from the group consisting of polyoxyethylene fatty acid ester, sorbitan fatty acid ester and polyoxyalkylenealkyl ether;
8) The agrochemically active microbial formulation according to any one of the items 1 to 5, wherein the surfactant is at least one kind of nonionic surfactant selected from the group consisting of polyoxyethylene fatty acid ester, sorbitan fatty acid ester and polyoxyalkylenealkyl ether, and the surfactant has an HLB of 7 to 12;
9) The agrochemically active microbial formulation according to any one of the items 1 to 8, wherein the agrochemically active microbe is at least one kind of microbe belonging to any one or more genera selected from the group consisting of *Paecilomyces, Beauveria, Metarhizium, Nomuraea, Verticillium, Hirsutella, Culicinomyces, Sorosporella, Tolypocladium, Fusarium, Trichoderma* and *Exserohilum;*

10) The agrochemically active microbial formulation according to any one of the items 1 to 8, wherein the agrochemically active microbe is pest controlling filamentous fungus;

11) The agrochemically active microbial formulation according to any one of the items 1 to 8, wherein the agrochemically active microbe is any one of the following pest controlling filamentous fungi:

(1) filamentous fungus of *Paecilomyces*, (2) filamentous fungus in which DNA encoding a nuclear 5.8S ribosomal RNA comprises the nucleotide sequence of SEQ ID NO:1 and DNA encoding a nuclear 28S ribosomal RNA comprises the nucleotide sequence of SEQ ID NO:2, (3) filamentous fungus belonging to *Paecilomyces tenuipes*, and (4) filamentous fungus which is *Paecilomyces tenuipes* T1 strain deposited at International Patent Organism Depositary, National Institute of Advanced Industrial Science and Technology as a deposition number FERM BP-7861;

12) A method of controlling a pest, comprising applying the agrochemically active microbial formulation as defined in any one of the items 1 to 11 to a pest, a habitat of a pest, or a plant to be protected from a pest (hereinafter, refereed to as a present control method in some cases);

13) A method of controlling a pest, comprising applying the agrochemically active microbial formulation as defined in any one of the items 1 to 11 to an agricultural or horticultural crop pest, a habitat of an agricultural or horticultural crop pest or an agricultural or horticultural crop to be protected from an agricultural or horticultural crop pest;

14) A process of producing an agrochemically active microbial formulation (hereinafter, referred to as a present process in some cases), comprising a step of mixing at least one kind of ester compound, a surfactant suitable for emulsifying the ester compound and an agrochemically active microbe, wherein the ester compound is selected from the following group:

(1) an ester compound which is liquid at 25° C., of monovalent fatty acid and polyhydric alcohol represented by the formula (II):

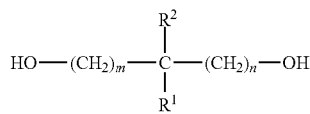

(II)

wherein $R^1$ and $R^2$ are the same or different, and represent a hydrogen atom, a methyl group, an ethyl group, a hydroxymethyl group or a 2-hydroxyethyl group, and m and n are the same or different, and represent 1 or 2, provided that $R^1$ and $R^2$ are not a hydrogen atom at the same time;

(2) an ester compound which is liquid at 25° C. of diglycerin and monovalent fatty acid, and (3) a diester compound which is liquid at 25° C., of adipic acid and monohydric alcohol; and 15) Use of at least one kind of ester compound as a medium for producing an agrochemically active microbial formulation, wherein the ester compound is selected from the following group:

(1) an ester compound which is liquid at 25° C., of monovalent fatty acid and polyhydric alcohol represented by the formula (III):

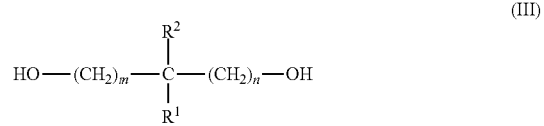

(III)

wherein $R^1$ and $R^2$ are the same or different, and represent a hydrogen atom, a methyl group, an ethyl group, a hydroxymethyl group or a 2-hydroxyethyl group, and m and n are the same or different, and represent 1 or 2, provided that $R^1$ and $R^2$ are not a hydrogen atom at the same time;

(2) an ester compound which is liquid at 25° C., of diglycerin and monovalent fatty acid, and (3) A diester compound which is liquid at 25° C., of adipic is acid and monohydric alcohol.

According to the present invention, an agrochemically active microbial formulation which exhibits a stable pest controlling effect with no harmful effect on a plant and has highly stable viability of the agrochemically active microbe can be provided.

DESCRIPTION OF THE INVENTION

The present invention will be explained in detail below.

Usually, the present formulation is suitably a formulation form such as a form termed oil-based flowable formulation.

The agrochemically active microbe used in the present formulation is a microbe having the pest controlling effect (in the present invention, the pest controlling effect includes insect pest controlling effect and/or plant disease controlling effect), additionally, includes a microbe having the weed controlling effect and a microbe having the plant growth regulating effect, for example.

Examples include one or more kinds of microbes belonging to any one or more genera selected from the group consisting of *Paecilomyces, Beauveri, Metarhizium, Nomuraea, Verticillium, Hirsutella, Culicinomyces, Sorosporella, Tolypocladium, Fusarium, Trichoderma* and *Exserohilum*.

As a preferable agrochemically active microbe, specifically, examples of an agrochemically active microbe belonging to *Paecilomyces* include microbes belonging to *Paecilomyces tenuipes, Paecilomyces fumosoroseus* and *Paecilomyces farinosus*. Specific examples include *Paecilomyces tenuipes* T1 strain deposited at International Patent Organism Depositary. National Institute of Advanced Industrial Science and Technology as a deposition number FERM BP-7861, *Paecilomyces tenuipes* ATCC44818, *Paecilomyces fumosoroseus* IFO8555, and *Paecilomyces fumosoroseus* IFO7072. Examples of an agrochemically active microbe belonging to *Beauveria* include microbes belonging to *Beauveria bassiana* and *Beauveria brongniartii*. Examples of an agrochemically active microbe belonging to *Metarhizium* include microbes belonging to *Metarhizium anisopliae, Metarhizium flavoviride* and *Metarhizium cylindrosporae*. Examples of an agrochemically active microbe belonging to *Nomuraea* include *Nomuraea rileyi*. Examples of an agrochemically active microbe belonging to *Verticillium* include *Verticillium lecanii*. Examples of an agrochemically active microbe belonging to *Fusarium* include microbes belonging to *Fusarium moniliforme, Fusarium oxysporum* and *Fusarium equiseti*. Examples of an agrochemically active microbe belonging to *Trichoderma* include microbes belonging to *Trichoderma aureoviride*. Examples of an agrochemically active microbe belonging to *Exserohilum* include microbes belonging to *Exserohilum monoceras*.

Among these agrochemically active microbes, a pest controlling filamentous fungus is more preferable. Specifically, example of the pest controlling filamentous fungus includes any one of the following pest controlling filamentous fungi:

(1) insect pest controlling filamentous fungus of *Paecilomyces*, (2) insect pest controlling filamentous fungus in which DNA encoding a nuclear 5.8S ribosomal RNA comprises the nucleotide sequence of SEQ ID NO:1 and DNA encoding a nuclear 28S ribosomal RNA comprises the nucleotide sequence of SEQ ID NO:2, (3) insect pest controlling filamentous fungus belonging to *Paecilomyces tenuipes*, and (4) pest controlling filamentous fungus which is *Paecilomyces tenuipes* T1 strain deposited at International Patent Organism Depositary, National Institute of Advanced Industrial Science and Technology as a deposition number FERM BP-7861.

These microbes may be separated from a nature, or may be purchased from a strain storage organization or the like.

When the agrochemically active microbe is a insect pest controlling filamentous fungus, for example, the fungus may be selected as follows.

When isolating from nature, first, a dead insect is taken in field, which has already stiffened and has a synnema growing from a body thereof. A conidium formed on said dead insect is touched with a platinum loop, and the platinum loop is rubbed on a solid culture medium such as SDY medium (composition: 1% (W/V) of peptone, 1% (W/V) of yeast extract, 2% (W/V) of glucose, 1.5% (W/V) of agar) and Czapek medium (composition: 0.3% (W/V) of $NaNO_3$, 0.1% (W/V) of $K_2HPO_4$, 0.05% (W/V) of $MgSO_4.7H_2O$, 0.05% (W/V) of KCl, 0.001% (W/V) of $FeSO_4.7H_2O$, 3% (W/V) of sucrose, 1.5 (W/V) of agar) in a line motion. The culture medium is cultured for few days at 25° C., and then an independent colony of a grown fungus is cut out and transferred to a new solid culture medium such as SDY medium and Czapek medium. The colony is further cultured at 25° C. A insect pest controlling filamentous fungus may be selected by identifying grown fungi (e.g., determining whether the filamentous fungus is categorized under the *Paecilomyces*) according to a method described in, for example, "Shokubutu Boeki (Plant Disease Protection)" a special issue No. 2, Tenteki-Biseibutu-No-Kenkyu-Shuho, published by Japan Plant Protection Association.

Next, the selected insect pest controlling filamentous fungus is determined whether it has an insecticidal activity. The selected insect pest controlling filamentous fungus (e.g., filamentous fungus of the genus *Paecilomyces*) is cultured on a solid culture medium such as SDY medium and Czapek medium at 25° C. A formed conidium is suspended in sterile water so that a concentration thereof is $1 \times 10^8$ CFU/mL. Ten insects belonging to the same species as of the dead insect from which the fungus has been isolated are dipped in the resultant suspension for 30 seconds and then kept under conditions of 25° C. and 100% humidity. If there is a dead insect 6 days after dipping, the fungus can be selected as an insect pest controlling filamentous fungus (e.g., insecticidal filamentous fungus of the genus *Paecilomyces*).

*Paecilomyces tenuipes* strain T1 was originally deposited under an accession number FERM P-18487 and has been deposited under the Budapest Treaty with the National Institute of Advanced Industrial Science and Technology International Patent Organism Depositary as an accession number FERM BP-7861 after transfer from the original deposition to the international deposition. The date of the original deposit was Aug. 29, 2001. The name of the microorganism is *paecilomyces tenuipes* T1. The address where the microorganism was deposited is AIST Tsukuba Central 6, 1-1, Higashi 1-chome Tsukuba-shi, Ibaraki-ken 305-8566, JAPAN. Mycological properties thereof are as follows.

(1) the Growth Rate (25° C., 7 Days)
  diameter of the colony: 25 to 30 mm (2% maltose extract agar medium plate), 25 to 30 mm (oatmeal agar medium plate)
(2) Color of the Front Surface of Colony
  white (2% maltose extract agar medium plate), white (oatmeal agar medium plate)
(3) Color of the Under Surface of Colony
  white (2% maltose extract agar medium plate), white to light yellow (oatmeal agar medium plate)
(4) Texture of the Front Surface of Colony
  wool-like to down-like
(5) Conidiophore
  smooth-surfaced branching and unstructured verticil
(6) Conidium
  smooth-surfaced elliptical to circular shape linkage, about 4 μm×about 2 μm
(7) Chlamydospore
  none (25° C., 9 day period)
(8) Nucleotide Sequence of DNA Encoding a Nuclear 5.8S Ribosomal RNA and Nucleotide Sequence of DNA Encoding a Nuclear 28S Ribosomal RNA
  the nucleotide sequence of DNA encoding a nuclear 5.8S ribosomal RNA is shown in SEQ ID NO: 1 and the nucleotide sequence of DNA encoding a nuclear 28S ribosomal RNA of is shown in SEQ ID NO: 2.

The agrochemically active microbe used in the present formulation can be prepared by culturing it in a liquid culture medium or a solid culture medium.

The culture medium used in culturing said fungus is not specifically limited as long as it allows said fungus to proliferate, and those can be used that are conventionally used for culturing microorganisms and contain appropriately a carbon source, a nitrogen source, an organic salt and an inorganic salt.

The liquid culture medium can be usually prepared by appropriately mixing water with a carbon source, a nitrogen source, an organic salt, an inorganic salt, vitamins and the like.

Examples of the carbon source used in the liquid culture medium include sugars such as glucose, dextrin and sucrose; sugar alcohols such as glycerol; organic acids such as fumaric acid, citric acid and pyruvic acid; animal oils; plant oils; molasses and the like. The amount of the carbon source contained in the culture medium is usually 0.1 to 20% (w/v).

Examples of the nitrogen source used in the liquid culture medium include natural organic nitrogen sources such as meat extract, peptone, yeast extract, malt extract, soybean powder, corn steep liquor, cotton seed powder, dried yeast and casamino acid; ammonium salts or nitrates of inorganic acids such as sodium nitrate, ammonium chloride, sodium sulfate and ammonium phosphate; ammonium salts of organic acids such as ammonium fumarate and ammonium citrate; urea; amino acids and the like. The amount of the nitrogen source contained in the culture medium is usually 0.1 to 30% (w/v).

Examples of the organic salt and the inorganic salt used in the liquid culture medium include chlorides, sulfates, acetates, carboxylates or phosphates of potassium, sodium, magnesium, iron, manganese, cobalt and zinc and the like, and more specifically, include sodium chloride, potassium chloride, magnesium sulfate, iron (I) sulfate, manganese sulfate, cobalt chloride, zinc sulfate, copper sulfate, sodium acetate, calcium carboxylate, sodium carboxylate, potassium phosphate monohydrate and potassium phosphate dehydrate and the like. The amount of the inorganic salt or organic salt contained in the culture medium is usually 0.0001 to 5% (w/v).

Examples of the vitamin include thiamine and the like.

Examples of the solid culture medium include main crops such as rice, wheat and the like and cereals such as maize, millet, barnyard grass, kaoliang, buckwheat and the like and sawdust, bagasse, rice hulls, wheat bran, seedpod, straw, corn cob, cotton seed lees, bean curd refuse, agar and gelatin and the like. Those may be used as a mixture of two or more of them. Also included are those which contain the carbon source, the nitrogen source, the organic salt, the inorganic salt and/or the vitamin and the like used in the liquid culture medium described above.

Specific examples of the culture medium used in culturing the agrochemically active microbe include liquid culture media such as 2% maltose extract liquid medium, oatmeal liquid medium, potato dextrose liquid medium, Sabouraud liquid medium and L-broth liquid medium and solid culture media such as rice, barley, wheat bran and an agar medium (2% maltose extract agar medium, oatmeal agar medium, potato dextrose agar medium, Sabouraud agar medium, L-broth agar medium and the like).

Cultivation of the microbe can be conducted according to methods conventionally utilized to culture microorganisms.

That is, examples of a method for culturing in a liquid culture medium include test tube shake culture, reciprocal culture, jar fermenter and tank culture, and examples of a method for culturing in a solid culture medium include stationary culture, which may be turned according to need.

The culture temperature may appropriately change in the range which allows the Fungus to grow, but is usually the range of 10° C. to 35° C., and preferably 15° C. to 35° C. The pH of the culture medium is usually the range of about 4 to 11, and preferably about 5 to 7. The culture period may change with the culturing conditions, but is usually in the range of about 1 day to about 2 months.

The microbe can be obtained by a method of centrifuging a culture fluid in which the microbe is cultured, a method of adding distilled water and the like to and scraping the microbe from the surface of a solid culture medium on which the microbe is cultured or a method of drying and grinding the solid culture medium and then fractionating with sieve.

A preferable state of the agrochemically active microbe used in the present formulation includes a state of a dry powder from a viewpoint of stability of the microbe. It is suitable that a water content of the dry powder is not more than 10% by weight, preferable not more than 7% by weight.

A preferable form of the agrochemically active microbe used in the present formulation is not particularly limited, but there is a preferable form for every kind of the agrochemically active microbe. Specifically, for example, in the case of *Paecilomyces, Beauveri, Metarhizium, Nomuraea, Verticillium, Hirsutella, Culicinomyces, Sorosporella, Tolypocladium, Fusarium, Trichoderma* and *Exserohilum*, generally, since their conidium has a hydrophobic surface, conidium is exemplified as a preferable form.

An amount of the agrochemically active microbe contained in the present formulation is not particularly limited as far as the present formulation is prepared so that necessary efficacy is obtained when applied, but is usually around 0.1 to 30% by weight, preferably around 0.5 to 20% by weight, more preferably around 1 to 15% by weight, particularly preferably around 1 to 10% by weight relative to a total weight of the present formulation. In addition, it is preferable that the agrochemically active microbe is usually contained at $10^3$ to $10^{13}$ CPU (CFU: colony forming unit) per gram of the present formulation.

The ester compound used in the present formulation (i.e., the present ester compound) refers to at least one kind of ester compound selected from the following group.

(1) An ester compound which is liquid at 25° C., of monovalent fatty acid and polyhydric alcohol represented by the formula (IV):

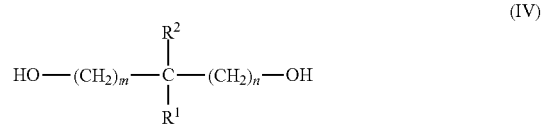

(IV)

wherein $R^1$ and $R^2$ are the same or different, and represent a hydrogen atom, a methyl group, an ethyl group, a hydroxylmethyl group or a 2-hydroxy group, and m and n are the same or different, and represent 1 or 2, provided that $R^1$ and $R^2$ are not a hydrogen atom at the same time (incidentally, it is preferable that the number of free hydroxyl groups in the ester compound is smaller), (2) An ester compound which is liquid at 25° C., of diglycerin $[O[CH_2CH(OH)CH_2OH]_2$ registered as CAS No. 627-82-7, also known as another name of Diglycerol)

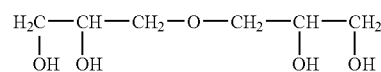

and monovalent fatty aid, and (3) A diester compound which is liquid at 25° C., of adipic acid [$HOOC(CH_2)_4COOH$ registered as CAS No. 124-04-9]

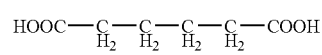

and monohydric alcohol.

The "polyhydric alcohol represented by the formula (I) (or the formula (II), (III) or (IV))" in the present invention may be unsaturated, and is preferably saturated. Preferable examples of the polyhydric alcohol include Pentaerythritol [$C(CH_2OH)_4$ registered as CAS No. 115-77-5, also known as Pentaerythrit,2,2-Bis(hydroxymethyl)-1,3-propanediol, Tetrakis(hydroxymethyl)methane, Tetramethylolomethane as another name],

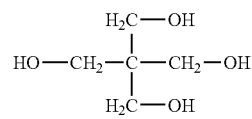

Trimethylolalkane [e.g. 2-alkyl-2-hydroxymethyl-1,3-propanediol, a representative of which is $C_5H_{12}O_3$ registered as CAS No. 77-85-0, and $C_6H_{14}O_3$ registered as CAS No. 77-99-6; wherein the "alkyl" includes, for example, lower alkyl (specifically, e.g. methyl, ethyl etc.)],

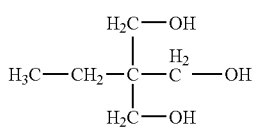

Neopentyl Glycol [HOCH$_2$C(CH$_3$)$_2$CH$_2$OH registered as CAS No. 126-30-7, also known as 2,2-dimethyl-1,3-propanediol as another name]

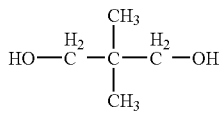

The "monovalent fatty acid" in the present invention may not be branched, or may be branched. In addition, the monovalent fatty acid may be unsaturated, and is preferably saturated. Further, it is suitable that the monovalent fatty acid is fatty acid having the number of carbon atoms of not less than 7 and not more than 18. Examples of such a monovalent fatty acid include specifically n-heptanoic acid, an isomer of n-heptanoic acid, n-octanoic acid, an isomer of n-octanoic acid (e.g. 2-ethylhexanoic acid), n-nonanoic acid, an isomer of n-nonanoic acid, n-decanoic acid (capric acid), an isomer of n-decanoic acid, n-undecanoic acid, an isomer of n-undecanoic acid, n-dodecanoic acid, an isomer of n-dodecanoic acid, n-tridecanoic acid, an isomer of n-tridecanoic acid, n-tetradecanoic acid, an isomer of n-tetradecanoic acid, n-pentadecanoic acid, an isomer of n-pentadecanoic acid, n-hexadecanoic acid, an isomer of n-hexadecanoic acid, n-heptadecanoic acid, an isomer of n-heptadecanoic acid, n-octadecanoic acid, and an isomer of n-octadecanoic acid. Inter alia, 2-ethylhexanoic acid which is an isomer of n-octanoic acid, an isomer of n-octadecanoic acid or n-decanoic acid (capric acid) is preferable.

The "monohydric alcohol" in the present invention may not be branched, or may be branched. In addition, the monohydric alcohol may be unsaturated, and is preferably saturated. Further, it is suitable that the monohydric alcohol is a monohydric alcohol having the number of carbon atoms of not less than 6 and not more than 18. Examples of such a monohydric alcohol include specifically n-hexyl alcohol, an isomer of n-hexyl alcohol, n-heptyl alcohol, an isomer of n-heptyl alcohol, n-octyl alcohol, an isomer of n-octyl alcohol (e.g. 2-ethylhexyl alcohol), n-nonyl alcohol, an isomer of n-nonyl alcohol (e.g. 5-nonyl alcohol), n-decyl alcohol, an isomer of n-decyl alcohol, n-undecyl alcohol, an isomer of n-undecyl alcohol, n-dodecyl alcohol, an isomer of n- dodecyl alcohol, n-tridecyl alcohol, an isomer of n-tridecyl alcohol, n-tetradecyl alcohol, an isomer of n-tetradecyl alcohol, n-pentadecyl alcohol, an isomer of n-pentadecyl alcohol, n-hexadecyl alcohol, an isomer of n-hexadecyl alcohol, n-heptadecyl alcohol, an isomer of n-heptadecyl alcohol, n-octadecyl alcohol, and an isomer of n-octadecyl alcohol (e.g. 2-heptylundecyl alcohol). Inter alia, preferable examples include 2-heptylundecyl alcohol.

Examples of a particularly preferable present ester compound include at least one king of ester compound selected from the following group.

(a) A tetraester compound which is liquid at 25° C., of pentaerythritol and 2-ethylhexanoic acid, (b) A triester compound which is liquid at 25° C., of trimethylolpropane and isomer of n-octadecanoic acid, (c) A diester compound which is liquid at 25° C., of neopentyl glycol and capric acid, (d) A tetraester compound which is liquid at 25° C., of diglycerin and isomer of n-octadecanoic acid, (e) A triester compound which is liquid at 25° C., of diglycerin and isomer of m-octadecanoic acid, and (f) A diester compound which is liquid at 25° C., of adipic acid and 2-heptylundecyl alcohol.

The present ester compound can be chemically synthesized by binding an acid and an alcohol by an ester reaction and, for example, in the case of a tetraester compound obtained by reacting pentaerythritol and 2-ethylhexanoic acid, the compound can be also purchased as a commercially available product (e.g. SALACOS 5408 (registered trademark) etc.) from The Nisshin OilliO Group, Ltd. In the case of a trimester compound obtained by reacting trimethylolpropane and an isomer of n-octadecanoic acid, the compound can be also purchased as a commercial available product (e.g. SALACOS 6318V (registered trademark) etc.) from The Nisshin OilliO Group, Ltd. In the case of a diester compound obtained by reacting neopentyl glycol and capric acid, the compound can be also purchased as a commercially available product (e.g. UNISTER H-210H (registered trademark) etc.) from NOF CORPORATION. In the case of a tetraester compound obtained by reacting diglycerin and an isomer of n-octadecanoic acid, the compound can be also purchased as a commercially available product (e.g. COSMOL 44V (registered trademark) etc.) from The Nisshin OilliO Group, Ltd. In the case of a triester compound obtained by reacting diglycerin and an isomer of n-octadecanoic acid, the compound can be also purchased as a commercially available product (e.g. COSMOL 43V (registered trademark) etc.) from The Nisshin OilliO Group, Ltd. In the case of a diester compound obtained by reacting adipic acid and isodecyl alcohol, the compound can be also purchased as a commercially available product (e.g. VINYCIZER 50 (registered trademark) etc.) from Kao Corporation. In the case of a diester compound obtained by reacting adipic acid and 2-heptylundecyl alcohol, the compound can be also purchased as a commercially available product (e.g. SALASCO 618 (registered trademark) etc.) from The Nisshin OilliO Group, Ltd.

An amount of the present ester compound contained in the present formulation is, for example, usually around 40 to 99.8% by weight, preferably around 60 to 98.5% by weight, more preferably around 75 to 98% by weight, particularly around 80 to 96% by weight relative to a total weight of the present formulation.

A viscosity of the present ester compound at 25° C. is usually not higher than 2000 mPa·s, preferably not higher than 1000 mPa·s, more preferably not higher than 500 mPa·s, particularly preferably not higher than 400 mPa·s. A method of measuring a viscosity may be any method as far as it is a method suitable for measuring a viscosity of an ester compound which is liquid at 25° C.

The present ester compound may be used alone, or by mixing two or more kinds. When used by mixing two or more kinds, each compound may be mixed arbitrarily.

When the present ester compound is used by mixing two or more kinds, an amount of the mixture of the present ester compounds contained in the present formulation is, for example, usually around 40 to 99.8% by weight, preferably around 60 to 98.5% by weight, more preferably around 75 to 98% by weight, particularly preferably around 80 to 96% by weight relative to a total weight of the present formulation.

The surfactant used in the present formulation is a surfactant suitable for emulsifying the present ester compound (i.e. present surfactant), and the surfactant dose not include the present ester compound, and is not particularly limited as far as it dose not adversely influence on the agrochemically active microbe contained in the present formulation, and a plant to be applied. The present surfactant may be used alone, or may be used by mixing two or more kinds of surfactants.

Examples of the surfactant suitable for emulsifying the present ester compound (i.e. present surfactant) include preferably a nonionic surfactant. Specific examples include nonionic surfactants such as dialkylsulfosuccinate, polyoxyethylene fatty acid ester, sorbitan fatty acid ester, sorbit fatty acid ester, polyoxyalkylenealkyl ether (e.g. polyoxyethylenealkyl ether, polyoxypropylenealkyl ether), polyoxyethylene hardened castor oil, polyoxyethylene fatty acid amide, sugar alcohol derivative, and silicone-based surfactant.

More preferably, examples include polyoxyethylene fatty acid ester and polyoxyethylenealkyl ether. Specifically, examples of polyoxyethylene fatty aid ester include PEG-NOL 14-O (registered trademark) (manufactured by TOHO Chemical Industry Co., Ltd.), and examples of polyoxyethylenealkyl ether include PEGNOL O-4 (registered trademark) (manufactured by TOHO Chemical Industry Co., Ltd.), PEGNOL O-6A (registered trademark) (manufactured by TOHO Chemical Industry Co., Ltd.), and PEGNOL 24-O (registered trademark) (manufactured by TOHO Chemical Industry Co., Ltd.).

Among the HLB of the nonionic surfactant used in the present formulation, the HLB which is more suitable in the present invention is determined by a kind and a content of the ester compound used in combination, and generally includes a range of 7 to 12.

A preferable range of the HLB possessed by at least one kind of nonionic surfactant selected from the group consisting of polyoxyethylene fatty acid ester, sorbitan fatty acid ester and polyoxyalkylenealkyl ether which are the nonionic surfactant used in a combination with the present ester compound is 7 to 10, more preferably 7 to 9. The HLB is calculated by the following calculating equation and, when as the present surfactant, two or more kinds of surfactants are used by mixing them, the HLB of each surfactant is obtained and, thereafter, the HLB of the surfactant mixture may be obtained as a sum of values that is obtained by multiplying the HLB obtained for each surfactant with an existing ratio.

$$HLB = (\text{molecular weight of hydrophilic part/molecular weight of surfactant}) \times 20$$

An amount of the present surfactant contained in the present formulation is, for example, usually around 0.1 to 30% by weight, preferably around 1 to 20% by weight, more preferably around 1 to 10% by weight, particularly preferably around 3 to 10% by weight.

A ratio by weight (part by weight) of each component contained in the present formulation to be blended in the formulation is, for example, such that present ester compound: present surfactant: agrochemically active microbe is usually 40 to 99.8 parts by weight: 0.1 to 30 parts by weight: 0.1 to 30 parts by weight, preferably 60 to 98.5 parts by weight: 1 to 20 parts by weight: 0.5 to 20 parts by weight, more preferably 75 to 98 parts by weight: 1 to 10 parts by weight: 1 to 15 parts by weight, particularly preferably 80 to 96 parts by weight: 3 to 10 parts by weight: 1 to 10 parts by weight.

In addition to the above components, further if necessary, as other component or a balance, a supplemental material which is usually used in agriculture, for example, a solid carrier, a liquid carrier, a liquid nature regulating agent (pH regulating agent etc.), a spreader, an extender, a wetting agent, a stabilizer, (antiseptic, drying agent, lyophilization preventing agent, coagulation preventing agent, antioxidant, ultraviolet absorbing agent, thickener), drift preventing agent and the like can be added to the present formulation in such a range that the pest controlling effect and the formulation property possessed by the agrochemically active microbe are not lost.

When these supplemental materials are added, a total of addition amounts thereof is usually not less than 0.1% by weight and not more than 50% by weight, preferably not less than 0.5% by weight and not more than 20% by weight relative to a total weight of the present formulation.

A conventional process for producing an agrochemical formulation can be applied to a process for producing the present formulation. For example, the present formulation can be produced by mixing fungal cells of the agrochemical microbe obtained by the aforementioned method, the present ester compound and the present surfactant and, further if necessary, other components or a supplemental material as a balance. Upon mixing, components may be mixed using a stirring machine such as a small magnetic stirrer, or may be mixed using a large stirring tank provided with various stirring wings which are generally utilized. The stirring tank may be provided with a baffle, if necessary.

Examples of a pest for which the present formulation has the pest controlling effect include pests such as the following agricultural or horticultural crop pests based on the pest controlling effect of the agrochemically active microbe used in the present formulation.

*Hemiptera*: planthoppers (Delphacidae) such as small brown planthopper (*Laodelphax striatellus*), brown rice planthopper (*Nilaparvata lugens*) and whitebacked rice planthopper (*Sogatella furcifera*); leafhoppers (Deltocephalidae) such as green rice leafhopper (*Nephotettix cincticeps*) and tea green leafhopper (*Empoasca onukii*); aphids (Aphididae) such as cotton aphid (*Aphis gossypii*), green peach aphid (*Myzus persicae*) and turnip aphid (*Lipaphis pseudobrassicae*); shield bugs (Pentatomidae): whiteflies (Aleyrodidae) such as greenhouse whitefly (*Trialeurodes vaporariorum*), sweetpotato whitefly (*Bemisia tabaci*) and silverleaf whitefly (*Bemisia argentifolii*); scales; lace bugs (Tingidae); psyllids (Psyllidae) and the like.

*Lepidoptera*: pyralid moths (Pyralidae) such as rice stem borer (*Chilo suppressalis*), rice leaf roller (*Cnaphalocrocis medinalis*), European corn borer (*Ostrinia nubilalis*) and *Parapediasia teterrella*; owlet moths (Noctuidae) such as common cutworm (*Spodoptera litura*), beet armyworm (*Spodoptera exigua*), oriental armyworm (*Pseudaletia separata*), cabbage armyworm (*Mamestra brassicae*), black cutworm (*Agrotis ipsilon*), *Trichoplusia* spp., *Heliothis* spp., *Helicoverpa* spp. (e.g., corn earworm (*Helicoverpa armigera*)), *Earias* spp. and *Autographa* spp. (e.g., beet semilooper (*Autographa nigrisigna*)); whites (Pieridae) such as common cabbageworm (*Pieris rapae crucivora*); yponomeutids (Yponomeutidae) such as diamondback moth (*Plutella xylostella*); tussock moths (Lymantriidae) such as oriental tussock moth (*Euproctis taiwana*), gypsy moth (*Lymantria dispar*), browntail moth (*Euproctis similis*); slug caterpillar moths (Limacodidae) such as *Scopelodes contracus*; tent caterpillar moths (Lasiocampidae) such as pine caterpillar (*Dendrolimus spectabilis*); leafroller moths (Tortricidae) such as summer fruit tortrix (*Adoxophyesorana fasciata*), oriental fruit moth (*Grapholita molesta*) and Codling moth (*Cydia pomonella*); Carposinidae such as peach fruit moth (*Carposina niponensis*); Lyonetildae such as Apple leafminer (*Lyonetia clerkella*); Gracillarlidae such as Apple leafminer (*Phyllonorycter ringoniella*); Phyllocnistidae such as citrus leafminer (*Phyllocnistis citrella*); *Yponomeuta* evonymella such as cabbage moth (*Plutella xylostella*); gelechiid moths (Gelechii) such as Pink Bollworm (*Pectinophora gossypiella*); tiger moths (Arctiidae); Tineidae and the like.

*Coleoptera*: leaf beetles (Chrysomelidae), chafers (Scarabaeidae), snout beetles (Curculionidae), leaf-rolling weevils (Attelabidae), Lady Beetles (Coccinelidae), Longhorn Beetles (Cerambycidae), Darkling Beetles (tenebrionidae) and the like.

*Thysanoptera*: thrips (Thripidae) such as the genus *Thrips* (e.g., melon thrips (*Thrips palmi*)), the genus *Frankliniella* (e.g., Western Flower *Thrips* (*Frankliniella occidentalis*)) and the genus *Sciltothrips* (e.g., yellow tea thrips (*Sciltothrips dorsalis*)); Tube-tailed *Thrips* (Phlaeothripidae) and the like.

*Orthoptera*: grasshoppers (ACRIDIDAE), mole crickets (Gryllotalpidae).

Rice plant disease: such as *Thanatephorus cucumeris, Pyricularia oryzae* and *Cochliovolus miyabeanus* of Rice plant.

Disease of wheat, barley, rye and oats: such as *Erysiphe graminis, Ustillago nuda, Septoria tritisi, Leptospharia nudorum, Pseudocercosporella herpotrichoides, Puccinia recondita, Puccinia graminis* and *Rhynchosporium secalis* of wheat, barley, rye and oats.

Pulse disease: such as *Cercospora arachidicola* of peanut, *Cercospora kikuchii* of soybean, *Ascochyta pisi* of pea. *Botrytis fabae* of broad bean, *Botrytis cinerea* and *Sclerotinia sclerotiorum* of pulse.

Disease of potato and crops for special use: such as *Phytophthora infestans* and *Alternaria salani* of potato, *Cercopora beticola* of sugar beet, *Pseudomonas solanacearum* of potato.

Vegetable disease: such as *Botrytis cinerea* and *Sclerotinia sclerotiorum* of vegetables such as solanaceous vegetable, cucurbitaceous vegetable, strawberry, lettuce and onion; *Cladosporium fulvum, Alternaria salani, Fusarium oxysporum* and *Pyrenochaeta lycopersici* of tomato; *Phytophthora infestans, Verticillium dahliae* and *Pseudomonas solanacearum* of tomato and eggplant; *Phytophthora capsici* of bell pepper; *Colletotrichum lagenarium, Mycosphaerella melonis, Sphaerotheca fuliginea, Fusarium oxysporum* and *Pseudoperonospora cubensis* of cucurbitaceous vegetable; *Puccinia allii* and *Sclerotinia allii* of leek; *Alternaria brassicae* of Chinese cabbage; *Alternaria dauci* of carrot; *Sphaerotheca humuli* and *Colletotrichum fragariae* of strawberry; *Alternaria brassicicola* of cabbage; *Peronospora brassicae* of vegetables and radish; *Peronospora spinaciae* of spinach; *Peronospora tabacina* of tobacco; and *Plasmopala nivea* of umbelliferous plant.

Flowers disease: such as *Botrytis cinerea* of flowers such as cyclamen, chrysanthemum, rose and notch-leaf sea lavender; *Spaerotheca pannosa* of rose; and *Puccinia horiana* of chrysanthemum.

Fruit tree disease: such as *Penicillium italicum, Diaporthe cltri, Penicillium digitatum, Penicllium italicum* of citrus; *Gymnosporangium asiaticum, Alternaria kikuchiana, Venturia nashicola, Venturia inaequalis, Alternaria mali* of pear; *Monilinia fructicola* of peach; and *Botrytis cinerea* and *Glomerella cingulata* of grape.

Turf disease: such as *Rhizoctonia solani, Curvularia sp, Helminthosporium sp, Puccinia zoysiae, Sclerotinia homoeocarpa, Fusarium, Rhizoctonia, Pythium* and *Typhula incarnata* of turf.

The present formulation can be usually used by applying to a pest such as an agricultural or horticultural crop pest, a habitat of a pest such as an agricultural or horticultural crop pest, or a plant such as an agricultural or horticultural crop (specifically, e.g. tomato, cabbage, cucumber, pumpkin, common bean, egg plant, bell pepper, radish, water melon, strawberry etc.) to be protected from a pest such as an agricultural or horticultural crop pest. When applied to a plant which should be protected from a pest, usually, the present formulation may be used by diluting with water to a concentration of $10^3$ to $10^{12}$ CFU/ml as an amount of cells of an agrochemically active microbe, and applying the diluted solution to a foliage of the plant.

The diluted solution may be used by applying to soil where the plant is growing. This application may be used when the agrochemically active microbe is a plant disease controlling filamentous fungus (specifically, soil-borne plant disease controlling filamentous fungus).

When the present formulation is applied to a pest, a habitat of a pest, or a plant to be protected from a pest, an application amount is usually $10^5$ to $10^{19}$ CFU, preferably $10^7$ to $10^{17}$ CFU as an amount of cells of the agrochemically active microbe used in the present formulation per 1000 m$^2$.

EXAMPLES

The following examples illustrate specifically the present invention, but the present invention is not limited to these examples.

Example 1

Production of the Present Formulation: 1

In a glass bottle, 93.0% by weight of SALACOS 5408 (manufactured by The Nisshin OilliO Group, Ltd.) and 5.0% by weight of Pegnol 24-O (manufactured by TOHO Chemical Industry Co., Ltd.) were charged and mixed well, and then added 2.0% by weight of a fungus powder obtained in Reference Example 3 and mixed to obtain the present formulation (1).

Example 2

Production of the Present Formulation: 2

In a glass bottle, 93.0% by weight of SALACOS 6318V (manufactured by The Nisshin OilliO Group, Ltd.) and 5.0% by weight of PEGNOL 24-O (manufactured by TOHO Chemical Industry Co., Ltd.) were charged and mixed well, and then added 2.0% by weight of a fungus powder obtained in Reference Example 3 and mixed to obtain the present formulation (2).

Example 3

Production of the Present Formulation: 3

In a glass bottle, 93.0% by weight of COSMOL 44V (manufactured by The Nisshin OilliO Group. Ltd.) and 5.0% by weight of PEGNOL 24-O (manufactured by TOHO Chemical Industry Co., Ltd.) were charged and mixed well, and then added 2.0% by weight of a fungus powder obtained in Reference Example 3 and mixed to obtain the present formulation (3).

Example 4

Production of the Present Formulation: 4

In a glass bottle, 93.0% by weight of COSMOL 43V (manufactured by The Nisshin OilliO Group, Ltd.) and 5.0% by weight of PEGNOL 24-O (manufactured by TOHO Chemical Industry Co. Ltd.) were charged and mixed well, and then added 2.0% by weight of a fungus powder obtained in Reference Example 3 and mixed to obtain the present formulation (4).

Example 5

Production of the Present Formulation: 5

In a glass bottle, 93.0% by weight of SALACOS 618 (manufactured by The Nisshin OilliO Group, Ltd.) and 5.0% by weight of PEGNOL 24-O (manufactured by TOHO Chemical Industry Co., Ltd.) were charged and mixed well, and then added 2.0% by weight of a fungal cell powder obtained in Reference Example 3 and mixed to obtain the present formulation (5).

Example 6

Production of the Present Formulation: 6

In a glass bottle, 85.0% by weight of UNISTER H-210R (manufactured by NOH CORPORATION) and 10.0% by weight of PEGNOL 24-O (manufactured by TOHO Chemical Industry Co., Ltd.) were charged and mixed well, and then added 5.0% by weight of a fungus powder obtained in Reference Example 3 and mixed to obtain the present formulation (6).

Example 7

Production of the Present Formulation: 7

In a glass bottle, 30.0% by weight of SALACOS 5408 (manufactured by The Nisshin OilliO Group, Ltd.), 25.0% by weight of COSMOL 44V (manufactured by The Nisshin OilliO Group, Ltd.), 30.0% by weight of UNISTER H-210R (manufactured by NOH CORPORATION) and 10.0% by weight of PEGNOL 24-O (manufactured by TOHO Chemical Industry Co., Ltd.) were charged and mixed well, and then added 5.0% by weight of a fungus powder obtained in Reference Example 3 and mixed to obtain the present formulation (7).

Example 8

Production of the Present Formulation: 8

In a glass bottle, 94.7% by weight of SALACOS 5408 (manufactured by The Nisshin OilliO Group. Ltd.) and 5.0% by weight of PEGNOL 24-O (manufactured by TOHO Chemical Industry Co., Ltd.) were charged and mixed well, and then added 0.3% by weight of a fungus powder obtained in Reference Example 3 and mixed to obtain the present formulation (8).

Example 9

Production of the Present Formulation: 9

In a glass bottle, 40.0% by weight of SALACOS 5408 (manufactured by The Nisshin OilliO Group, Ltd.), 45.0% by weight of COSMOL 44V (manufactured by The Nisshin OilliO Group, Ltd.) and 10.0% by weight of PEGNOL 24-O (manufactured by TOHO Chemical Industry Co., Ltd.) were charged and mixed well, and then added 5.0% by weight of a fungus powder obtained in Reference Example 3 and mixed to obtain the present formulation (9).

Test Example 1

Stability of Agrochemically Active Microbe Viability in the Present Formulation

Each 20 mg of a sample was taken from each of the present formulations (1) to (7), and added with 20 mL of sterile diluted water to prepare a suspension. The suspension was diluted to an appropriate concentration with the sterile diluted water. 100 μL of the resultant diluted suspension was dropped and spread on a potato dextrose agar medium, and cultured for 3 days at 25° C. After cultivation, a viable count of the agrochemically active microbe in the formulation was determined by counting grown colonies. At the same time, each of the present formulations (1) to (7) was placed in a glass screw cap bottle and closed, and then stored in dark for 2, 4 or 8 weeks at 40° C. 20 mg of a sample was taken from each of the stored present formulations (1) to (7), and added with 20 mL of sterile diluted water to prepare a suspension. The suspension was diluted to an appropriate concentration with the sterile diluted water. 100 μL of the resultant diluted suspension was dropped and spread on a potato dextrose agar medium, and cultured for 3 days at 25° C. After cultivation, a viable count of the agrochemically active microbe in the formulation was determined by counting grown colonies. The sterile diluted water used was prepared by adding Shin Lino (Nihon Nohyaku Co., Ltd.) and Silwet L-77 (Nippon Unica Co.) in a concentration of 0.1% (w/v) each to an aqueous solution of 0.85% (w/v) of sodium chloride, and sterilizing. Time course of the viable count of the agrochemically active microbe of each of the present formulations (1) to (7) from storage initiation to storage 8 weeks is shown in Table 1.

TABLE 1

| Storage term | Viable count (CFU/g) | | | |
|---|---|---|---|---|
| | Preparation day | 2 weeks | 4 weeks | 8 weeks |
| Present formulation (1) | $1.5 \times 10^9$ | $8.3 \times 10^8$ | $5.8 \times 10^8$ | $2.7 \times 10^8$ |
| Present formulation (2) | $1.5 \times 10^9$ | $1.5 \times 10^9$ | $4.1 \times 10^8$ | $2.1 \times 10^8$ |
| Present formulation (3) | $1.7 \times 10^9$ | $1.7 \times 10^9$ | $4.3 \times 10^8$ | $1.8 \times 10^8$ |
| Present formulation (4) | $1.4 \times 10^9$ | $5.7 \times 10^8$ | $2.6 \times 10^8$ | $8.2 \times 10^7$ |
| Present formulation (5) | $1.6 \times 10^9$ | $1.6 \times 10^9$ | $3.7 \times 10^8$ | $2.4 \times 10^8$ |
| Present formulation (6) | $5.1 \times 10^9$ | $3.4 \times 10^9$ | $2.8 \times 10^9$ | $1.7 \times 10^9$ |
| Present formulation (7) | $5.0 \times 10^9$ | $3.5 \times 10^9$ | $3.6 \times 10^9$ | $1.9 \times 10^9$ |

Test Example 2

Emulsification Test of Present Formulation 230 mL of water of hardness 3 was charged into a 250 mL cylinder with a fitted stopper. The cylinder was stopped up with the stopper, and then allowed to stand for 30 minutes or longer at 20° C. in a thermostat bath. 500 mg each of the present formulations (1) to (7) was added to individual cylinders, and then each of these cylinders was adjusted to 250 mL by adding water of hardness 3 at 20° C. The cylinder was stopped up with the stopper, and then turned upside down ten times for 20 seconds, and then allowed to stand at 20° C. in a thermostat bath. After 30 minutes, the cylinder was taken out from the thermostat bath, and the emulsified state was observed. Results are shown in Table 2.

TABLE 2

| | Emulsified state |
|---|---|
| Present formulation (1) | Uniformly emulsified |
| Present formulation (2) | Uniformly emulsified |
| Present formulation (3) | Uniformly emulsified |
| Present formulation (4) | Uniformly emulsified |
| Present formulation (5) | Uniformly emulsified |
| Present formulation (6) | Uniformly emulsified |
| Present formulation (7) | Uniformly emulsified |

Test Example 3

Phytotoxicity Test of Present Formulation

In a 100 ml glass beaker, 1 g of each of the present formulations (1) to (7) was charged and added 100 ml of distilled water, and then stirred for 3 minutes using a magnetic stirrer to obtain a test solution.

Cucumber, *Cucumis sativus* (variety: *Sagamihanpaku*) from which fourth true leaf or more had been excised, and tomato, *Lycopersicon esculentum* (variety: *Patio*) with 3 to 4 of true leaves were used as test plants, and a sufficient amount of the test solution was applied to a surface and a back of the plant leaves. The test plants after treatment were transferred into a greenhouse, and pots of the plants were soaked in an aqueous fertilizer during a test term. After treatment, growth and injury of the plants were observed periodically and, seven days after treatment (cucumber) or fourteen days after treatment (tomato), the plant injury was recorded at four levels (−: no injury, ±: injury, or symptom regarded as injury is recognized, but not practically problematic, +: injury is recognized, and practically problematic, ++: died). Average temperature and humidity during the test term were 24° C. and 30 to 40% Rh. Results are shown in Table 3.

TABLE 3

| | Injury on cucumber (7 days after treatment) | Injury on tomato (14 days after treatment) |
|---|---|---|
| Present formulation (1) | −: No injury | −: No injury |
| Present formulation (2) | −: No injury | −: No injury |
| Present formulation (3) | −: No injury | −: No injury |
| Present formulation (4) | −: No injury | −: No injury |
| Present formulation (5) | −: No injury | −: No injury |
| Present formulation (6) | −: No injury | −: No injury |
| Present formulation (7) | −: No injury | −: No injury |

Test Example 4

Pest Controlling Activity Test of Present Formulation

Adult sweetpotato whiteflies (*Bemisla tabaci* (Biotype B)) were released on cabbage, *Brassica oleracea* (variety: *Green Ball*) with 3 to 4 of true leaves. One day after the release, adults were removed and eggs were obtained on cabbage leaves. Cultivation was performed for 2 weeks under the condition of a temperature of 25° C. and a humidity of around 50% Rh to a low eggs of *Bemisia tabaci* to hatch on cabbage leaves. The number of *Bemisia tabaci* larvae hatched on cabbage leaves was counted, and this was used as the number of larvae before test solution applying. Then, in a 100 ml of a glass beaker, each 200 mg of each of the present formulations (1) to (7) was taken and added 100 ml of distilled water, and then stirred for 3 minutes using a magnetic stirrer to obtain a test solution. A sufficient amount of the test solution was applied on a surface and a back of cabbage leaves on which *Bemisia tabaci* had been hatched. After the application, cabbage was air-dried and cultivated for 1 week under the condition of a temperature of 25° C. and a humidity of not less than 95% Rh. The number of *Bemisia tabaci* larvae alive on the cabbage leaves was counted, and used as the number of alive larvae one week after test solution application. The mortality one week after test solution application was calculated from the following calculation equation, and the pest controlling effect was assessed at 4 levels (A: stably effective (mortality is 80% or more), B: effective (mortality is not less than 60% and less than 80%), C: insufficiently effective (mortality is not less than 40% and less than 60%), D: not effective (mortality is less than 40%)) based on the calculated mortality. Results are shown in Table 4.

Mortality one week after test solution application (%)=(number of larvae before test solution application−number of larvae alive one week after test solution application)÷(number of larvae before test solution application)×100

TABLE 4

| | pest controlling effect one week after test solution application |
|---|---|
| Present formulation (1) | A: Stably effective |
| Present formulation (1) | A: Stably effective |
| Present formulation (1) | A: Stably effective |
| Present formulation (1) | A: Stably effective |
| Present formulation (1) | A: Stably effective |
| Present formulation (1) | A: Stably effective |
| Present formulation (1) | A: Stably effective |

Reference Example 1

Isolation of an Agrochemically Active Microbe of the Genus *Paecilomyces*

A dead insect is taken in field, which has already stiffened and has a synnema growing from a body thereof. A conidium formed on said dead insect is touched with a platinum loop, and the platinum loop is rubbed on a SDY medium so as to draw a line. The culture medium is cultured for few days at 25° C., and then an independent colony of a grown fungus is cut out and transferred to a new SDY medium. The colony is further cultured at 25° C.

Among the resultant fungi, a fungus having the following properties a) to h) is selected as a filamentous fungus of the genus *Paecilomyces*.

a) A vegetative hyphae has a septum.
b) There is no sexual reproduction.
c) A conidium is not formed in a picnidium, a pot-like apparatus, but is an exoconidium.
d) A conidium is a phiaoconidium formed from a phialide apex, dry and catenulate.
e) A conidiophore has no microcystis on the top thereof.
f) A phialide is not arranged in a palisade form on a coremium.
g) catenulate conida do not form a bundle.
h) the phialide has a clear, deformed or lax verticillate neck.

Next, the selected filamentous fungus of the genus *Paecilomyces* is cultured in a SDY medium at 25° C. A formed conidium is suspended in sterile water so that a concentration thereof is $1 \times 10^8$ CFU/mL. Ten insects belonging to the same species as of the dead insect from which the fungus has been isolated are dipped in the resultant suspension for 30 seconds, and then reared under conditions of 25° C. and 100% humidity. If there is a dead insect 6 days after dipping, the fungus can be selected as an agrochemically active microbe of the genus *Paecilomyces*.

Reference Example 2

Preparation of an Agrochemically Active Microbe 1

In a 500 mL flask, a fungus body of Paecilomyces tenuipes Ti strain, which was previously cultured in potato dextrose agar medium (Difco Laboratories), was inoculated to 100 mL of potato dextrose medium (Difco Laboratories), and then cultured with shaking for 3 days at 25° C. to obtain a culture. Next, 80 g of sterilized bran was mixed with 160 ml of sterilized water and inoculated with 20 ml of the above culture, and then cultured for 14 days with intermittent irradiating (light condition: 14 hours in a row/day; dark condition: 10 hours in a row/day) with a light (at an illuminance of 2,000 to 3,000 lux), under the condition of a temperature of 25° C. and a humidity of 90% RH. After the cultivation, the bran on which fungus bodies (containing many conidia) were formed was dried. The dried bran and 5 agate balls of 20 mm diameter were placed in a standard sieve according to JIS (JIS Z 8801: a 60-mesh sieve was used), stacked on a standard sieve according to JIS (JIS Z 8801: 100- and 200-mesh sieves were used), and then shaken for 10 minutes on an automated sieve shaker (Fritsch GmbH) to obtain 2.0 g of fungus powder in a fraction not more than 200-mesh.

Reference Example 3

Preparation of an Agrochemically Active Microbe 2

In a 500 mL flask, a fungus body of *Paecilomyces tenuipes* T1 strain, which was previously cultured in potato dextrose agar medium (Difco Laboratories), was inoculated to 100 mL of potato dextrose medium (Difco Laboratories), and then cultured with shaking for 3 days at 25° C. to obtain a culture. Next, 80 g of flaked barley with the seed coat (Matsukage Seibaku Co., ltd.) was pre-crushed to particles having a diameter of 1 to 5 mm by a hand crusher HC-1 (Osaka Chemical Co., Ltd.), and then sterilized in an autoclave. The product was placed in a sterilized PET transparent tray (length: 310 mm, width: 220 mm, height: 80 mm), and then added and mixed with 20 g of the culture and 100 g of sterile water. The tray was covered with a piece of sterile cloth, and cultured for 17 days with continuously irradiating with a light at an illuminance of 6,000 lux, in an environmental control room of a temperature 25° C. and a humidity 90% RH. After cultivation, the flaked barley with the seed coat on which fungus bodies (containing many conidia) was dried. The dried flaked barley with the seed coat and 5 agate balls of 20 mm diameter were placed in a standard sieve according to JIS (JIS Z 8801: a 60-mesh sieve was used), stacked on a standard sieve according to JIS (JIS Z 8801: 100- and 200-mesh sieves were used), and then shaken for 10 minutes on an automated sieve shaker (Fritsch GmbH) to obtain 2 g of fungus powder in a fraction not more than 200-mesh, which contained $1 \times 10^{11}$ CFU/g of the fungus body of T1 strain.

Reference Example 4

Preparation of an Agrochemically Active Microbe 3

In a 500 mL flask, a fungus body of plant disease controlling filamentous fungus of the genus *Fusarium*, which was previously cultured in potato dextrose agar medium (Difco Laboratories), is inoculated to 100 mL of potato dextrose medium (Difco Laboratories), and then cultured with shaking for 3 days at 25° C. to obtain a culture. Next, 80 g of sterilized bran (Masuda Flour Milling Co., ltd.) is placed in a sterilized PET transparent tray (length: 310 mm, width: 220 mm, height: 80 mm), and then added and mixed with 20 g of the culture and 100 g of sterile water. The tray is covered with a piece of sterile cloth, and cultured for 14 days with continuously irradiating with a light at an illuminance of 6,000 lux, in an environmental control room of a temperature 25° C. and a humidity 90% RH. After cultivation, the bran on which fungus bodies (containing many conidia) is formed is dried. The dried bran and 5 agate balls of 20 mm diameter are placed in a standard sieve according to JIS (JIS Z 8801: a 60-mesh sieve was used), stacked on a standard sieve according to JIS (JIS Z 8801: 100- and 200-mesh sieves were used), and then shaken for 10 minutes on an automated sieve shaker (Fritsch GmbH) to obtain 2 g of fungus powder in a fraction not more than 200-mesh, which contained $1 \times 10^{11}$ CFU/g of the fungus body of the above plant disease controlling filamentous fungus.

What is claimed is:

1. An agrochemically active microbial formulation, comprising at least one ester compound, a surfactant suitable for emulsifying the at least one ester compound and an agrochemically active microbe, wherein the at least one ester compound is selected from the following group:
   (a) an ester compound which is liquid at 25° C., of a monovalent fatty acid and a polyhydric alcohol represented by the formula (I):

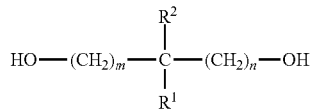

wherein $R^1$ and $R^2$ are the same or different, and represent a hydrogen atom, a methyl group, an ethyl group, a hydroxymethyl group or a 2-hydroxyethyl group, and m and n are the same or different, and represent 1 or 2, provided that $R^1$ and $R^2$ are not a hydrogen atom at the same time;
   (b) an ester compound which is liquid at 25° C., of diglycerin and a monovalent fatty acid; and
   (c) a diester compound which is liquid at 25° C., of adipic acid and a monohydric alcohol,
   wherein the at least one ester compound is present in an amount of 40 to 99.8% by weight of the total weight of the agrochemically active microbial formulation.

2. An agrochemically active microbial formulation, comprising at least one ester compound, a surfactant suitable for emulsifying the at least one ester compound and an agrochemically active microbe, wherein the at least one ester compound is selected from the following group:
   (a) an ester compound which is liquid at 25° C., of a monovalent fatty acid and a polyhydric alcohol represented by the formula (I):

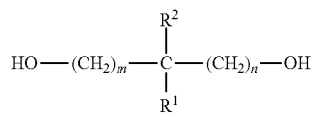

wherein $R^1$ and $R^2$ are the same or different, and represent a hydrogen atom, a methyl group, an ethyl group, a hydroxymethyl group or a 2-hydroxyethyl group, and m and n are the same or different, and represent 1 or 2, provided that $R^1$ and $R^2$ are not a hydrogen atom at the same time;
   (b) an ester compound which is liquid at 25° C., of diglycerin and a monovalent fatty acid, wherein the monovalent fatty acid is 2-ethylhexanoic acid, an isomer of n-octadecanoic acid, or capric acid,
   wherein the at least one ester compound is present in an amount of 40 to 99.8% by weight of the total weight of the agrochemically active microbial formulation.

3. The agrochemically active microbial formulation according to claim 1, wherein the monohydric alcohol is 2-heptylundecyl alcohol.

4. The agrochemically active microbial formulation according to claim 1, wherein the surfactant is a nonionic surfactant.

5. The agrochemically active microbial formulation according to claim 1, wherein the surfactant is at least one nonionic surfactant selected from the group consisting of polyoxyethylene fatty acid ester, sorbitan fatty acid ester and polyoxyalkylenealkyl ether.

6. The agrochemically active microbial formulation according to claim 1, wherein the surfactant is at least one nonionic surfactant selected from the group consisting of polyoxyethylene fatty acid ester, sorbitan fatty acid ester and polyoxyalkylenealkyl ether, and the surfactant has a hydrophile-lipophile balance (HLB) of 7 to 12.

7. The agrochemically active microbial formulation according to claim 1, wherein the agrochemically active microbe is at least one microbe belonging to any one or more genera selected from the group consisting of *Paecilomyces, Beauveria, Metarhizium, Nomuraea, Verticillium, Hirsutella, Culicinomyces, Sorosporella, Tolypocladium, Fusarium, Trichoderma* and *Exserohilum.*

8. The agrochemically active microbial formulation according to claim 1, wherein the agrochemically active microbe is a pest controlling filamentous fungus.

9. The agrochemically active microbial formulation according to claim 1, wherein the agrochemically active microbe is any one of the following pest controlling filamentous fungi:
(a) filamentous fungus of *Paecilomyces,*
(b) filamentous fungus in which DNA encoding a nuclear 5.8S ribosomal RNA comprises the nucleotide sequence of SEQ ID NO: 1 and DNA encoding a nuclear 28S ribosomal RNA comprises the nucleotide sequence of SEQ ID NO:2,
(c) filamentous fungus belonging to *Paecilomyces tenuipes,* and
(d) filamentous fungus which is *Paecilomyces tenuipes* T1 strain deposited at International Patent Organism Depositary, National Institute of Advanced Industrial Science and Technology as a deposition number FERM BP-7861.

10. A method of controlling a pest, comprising applying the agrochemically active microbial formulation as defined in claim 1 to a pest, a habitat of a pest, or a plant to be protected from a pest.

11. A method of controlling a pest, comprising applying the agrochemically active microbial formulation as defined in claim 1 to an agricultural or horticultural crop pest, a habitat of an agricultural or horticultural crop pest or an agricultural or horticultural crop to be protected from an agricultural or horticultural crop pest.

12. A process of producing an agrochemically active microbial formulation, comprising a step of mixing at least one ester compound, a surfactant suitable for emulsifying the at least one ester compound and an agrochemically active microbe, wherein the at least one ester compound is selected from the following group:
(a) an ester compound which is liquid at 25° C., of a monovalent fatty acid and a polyhydric alcohol represented by the formula (I):

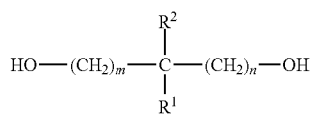

wherein $R^1$ and $R^2$ are the same or different, and represent a hydrogen atom, a methyl group, an ethyl group, a hydroxymethyl group or a 2-hydroxyethyl group, and m and n are the same or different, and represent 1 or 2, provided that $R^1$ and $R^2$ are not a hydrogen atom at the same time;

(b) an ester compound which is liquid at 25° C., of diglycerin and a monovalent fatty acid, and
(c) a diester compound which is liquid at 25° C., of adipic acid and a monohydric alcohol, wherein the at least one ester compound is present in an amount of 40 to 99.8% by weight of the total weight of the agrochemically active microbial formulation.

13. The process of producing an agrochemically active microbial formulation of claim 12, wherein the at least one ester compound is present in an amount of from 60 to 98.5% by weight of the total weight of the agrochemically active microbial formulation.

14. The process of producing an agrochemically active microbial formulation of claim 12, wherein the at least one ester compound is present in an amount of from 75 to 98% by weight of the total weight of the agrochemically active microbial formulation.

15. The process of producing an agrochemically active microbial formulation of claim 12, wherein the at least one ester compound is present in an amount of from 80 to 96% by weight of the total weight of the agrochemically active microbial formulation.

16. The agrochemically active microbial formulation of claim 1, wherein the at least one ester compound is present in an amount of from 60 to 98.5% by weight of the total weight of the agrochemically active microbial formulation.

17. The agrochemically active microbial formulation of claim 1, wherein the at least one ester compound is present in an amount of from 75 to 98% by weight of the total weight of the agrochemically active microbial formulation.

18. The agrochemically active microbial formulation of claim 1, wherein the at least one ester compound is present in an amount of from 80 to 96% by weight of the total weight of the agrochemically active microbial formulation.

19. An agrochemically active microbial formulation, comprising at least one ester compound, a surfactant suitable for emulsifying the ester compound and an agrochemically active microbe, wherein the at least one ester compound is selected from the following group:
(1) an ester compound which is liquid at 25° C., of a monovalent fatty acid and a polyhydric alcohol represented by the formula (I):

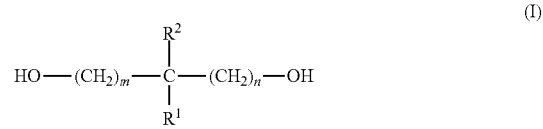

wherein $R^1$ and $R^2$ are the same or different, and represent a hydrogen atom, a methyl group, an ethyl group, a hydroxymethyl group or a 2-hydroxyethyl group, and m and n are the same or different, and represent 1 or 2, provided that $R^1$ and $R^2$ are not a hydrogen atom at the same time; and
(2) an ester compound which is liquid at 25° C., of diglycerin and a monovalent fatty acid,
wherein the monovalent fatty acid is 2-ethylhexanoic acid, an isomer of n-octadecanoic acid, or capric acid,
wherein the at least one ester compound is present in an amount of 40 to 99.8% by weight of the total weight of the agrochemically active microbial formulation.

20. An agrochemically active microbial formulation according to claim 19, wherein the polyhydric alcohol represented by the formula (I) is pentaerythritol, trimethylolalkane or neopentyl glycol.

21. The agrochemically active microbial formulation according to claim 19, wherein the surfactant is a nonionic surfactant.

22. The agrochemically active microbial formulation according to claim 19, wherein the surfactant is at least one nonionic surfactant selected from the group consisting of polyoxyethylene fatty acid ester, sorbitan fatty acid ester and polyoxyalkylenealkyl ether.

23. The agrochemically active microbial formulation according to claim 19, wherein the surfactant is at least one nonionic surfactant selected from the group consisting of polyoxyethylene fatty acid ester, sorbitan fatty acid ester and polyoxyalkylenealkyl ether, and the surfactant has a hydrophile-lipophile balance (HLB) of 7 to 12.

24. The agrochemically active microbial formulation according to claim 19, wherein the agrochemically active microbe is at least one microbe belonging to any one or more genera selected from the group consisting of *Paecilomyces, Beauveria, Metarhizium, Nomuraea, Verticillium, Hirsutella, Culicinomyces, Sorosporella, Tolypocladium, Fusarium, Trichoderma* and *Exserohilum*.

25. The agrochemically active microbial formulation according to claim 19, wherein the agrochemically active microbe is a pest controlling filamentous fungus.

26. The agrochemically active microbial formulation according to claim 1, wherein the agrochemically active microbe is any one of the following pest controlling filamentous fungi:

(a) filamentous fungus of *Paecilomyces*, (b) filamentous fungus in which DNA encoding a nuclear 5.8S ribosomal RNA comprises the nucleotide sequence of SEQ ID NO: 1 and DNA encoding a nuclear 28S ribosomal RNA comprises the nucleotide sequence of SEQ ID NO:2, (c) filamentous fungus belonging to *Paecilomyces tenuipes,* and (d) filamentous fungus which is *Paecilomyces tenuipes* T1 strain deposited at International Patent Organism Depositary, National Institute of Advanced Industrial Science and Technology as a deposition number FERM BP-7861.

27. A method of controlling a pest, comprising applying the agrochemically active microbial formulation as defined in claim 19 to a pest, a habitat of a pest, or a plant to be protected from a pest.

28. A method of controlling a pest, comprising applying the agrochemically active microbial formulation as defined in claim 19 to an agricultural or horticultural crop pest, a habitat of an agricultural or horticultural crop pest or an agricultural or horticultural crop to be protected from an agricultural or horticultural crop pest.

29. A process of producing an agrochemically active microbial formulation, comprising a step of mixing at least one ester compound, a surfactant suitable for emulsifying the at least one ester compound and an agrochemically active microbe, wherein the at least one ester compound is selected from the following group:

(a) an ester compound which is liquid at 25° C., of monovalent fatty acid and polyhydric alcohol represented by the formula (I):

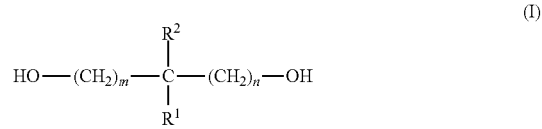

wherein $R^1$ and $R^2$ are the same or different, and represent a hydrogen atom, a methyl group, an ethyl group, a hydroxymethyl group or a 2-hydroxyethyl group, and m and n are the same or different, and represent 1 or 2, provided that $R^1$ and $R^2$ are not a hydrogen atom at the same time;

(b) an ester compound which is liquid at 25° C., of diglycerin and a monovalent fatty acid wherein the monovalent fatty acid is 2-ethylhexanoic acid, an isomer of n-octadecanoic acid, or capric acid, and wherein the at least one ester compound is present in an amount of 40 to 99.8% by weight of the total weight of the agrochemically active microbial formulation.

30. An agrochemically active microbial formulation, comprising at least one ester compound, a surfactant suitable for emulsifying the at least one ester compound and an agrochemically active microbe, wherein the at least one ester compound is selected from the following group:

(a) a tetraester compound which is liquid at 25° C., of pentaerythritol and 2-ethylhexanoic acid, (b) a triester compound which is liquid at 25° C., of trimethylolpropane and an isomer of n-octadecaneoctadecanoic acid, (c) a diester compound which is liquid at 25° C., of neopentyl glycol and capric acid, (d) a tetraester compound which is liquid at 25° C., of diglycerin and an isomer of n-octadecanoic acid, (e) a triester compound which is liquid at 25° C., of diglycerin and an isomer of n-octadecanoic acid, and (f) a diester compound which is liquid at 25° C., of adipic acid and 2-heptylundecyl alcohol, wherein the at least one ester compound is present in an amount of 40 to 99.8% by weight of the total weight of the agrochemically active microbial formulation.

31. The agrochemically active microbial formulation according to claim 30, wherein the surfactant is a nonionic surfactant.

32. The agrochemically active microbial formulation according to claim 30, wherein the surfactant is at least one nonionic surfactant selected from the group consisting of polyoxyethylene fatty acid ester, sorbitan fatty acid ester and polyoxyalkylenealkyl ether.

33. The agrochemically active microbial formulation according to claim 30, wherein the surfactant is at least one nonionic surfactant selected from the group consisting of polyoxyethylene fatty acid ester, sorbitan fatty acid ester and polyoxyalkylenealkyl ether, and the surfactant has a hydrophile-lipophile balance (HLB) of 7 to 12.

34. The agrochemically active microbial formulation according to claim 30, wherein the agrochemically active microbe is at least one microbe belonging to any one or more genera selected from the group consisting of *Paecilomyces, Beauveria, Metarhizium, Nomuraea, Verticillium, Hirsutella, Culicinomyces, Sorosporella, Tolypocladium, Fusarium, Trichoderma* and *Exserohilum*.

35. The agrochemically active microbial formulation according to claim 30, wherein the agrochemically active microbe is a pest controlling filamentous fungus.

36. The agrochemically active microbial formulation according to claim 1, wherein the agrochemically active microbe is any one of the following pest controlling filamentous fungi:
(a) filamentous fungus of *Paecilomyces,*
(b) filamentous fungus in which DNA encoding a nuclear 5.8S ribosomal RNA comprises the nucleotide sequence of SEQ ID NO: 1 and DNA encoding a nuclear 28S ribosomal RNA comprises the nucleotide sequence of SEQ ID NO:2,
(c) filamentous fungus belonging to *Paecilomyces tenuipes,* and
(d) filamentous fungus which is *Paecilomyces tenuipes* T1 strain deposited at International Patent Organism Depositary, National Institute of Advanced Industrial Science and Technology as a deposition number FERM BP-7861.

37. A method of controlling a pest, comprising applying the agrochemically active microbial formulation as defined in claim 30 to a pest, a habitat of a pest, or a plant to be protected from a pest.

38. A method of controlling a pest, comprising applying the agrochemically active microbial formulation as defined in claim 30 to an agricultural or horticultural crop pest, a habitat of an agricultural or horticultural crop pest or an agricultural or horticultural crop to be protected from an agricultural or horticultural crop pest.

39. A process of producing an agrochemically active microbial formulation, comprising a step of mixing at least one ester compound, a surfactant suitable for emulsifying the at least one ester compound and an agrochemically active microbe, wherein the at least one ester compound is selected from the following group:
(a) a tetraester compound which is liquid at 25° C., of pentaerythritol and 2-ethylhexanoic acid,
(b) a triester compound which is liquid at 25° C., of trimethylolpropane and an isomer of n-octadecanoic acid,
(c) a diester compound which is liquid at 25° C., of neopentyl glycol and capric acid,
(d) a tetraester compound which is liquid at 25° C., of diglycerin and an isomer of n-octadecanoic acid,
(e) a triester compound which is liquid at 25° C., of diglycerin and an isomer of n-octadecanoic acid, and
(f) a diester compound which is liquid at 25° C., of adipic acid and 2-heptylundecyl alcohol,
wherein the at least one ester compound is present in an amount of 40 to 99.8% by weight of the total weight of the agrochemically active microbial formulation.

* * * * *

SEQUENCE LISTING

<160> NUMBER OF SEQ ID NOS: 2

<210> SEQ ID NO 1
<211> LENGTH: 156
<212> TYPE: DNA
<213> ORGANISM: Paecilomyces tenuipes

<400> SEQUENCE: 1

-continued

```
aactttcaac aacggatctc ttggttctgg catcgatgaa gaacgcagcg aaatgcgata        60
cgtaatgtga attgcagaat tccgtgaatc atcgaatctt tgaacgcaca ttgcgcccgc       120
cagcattctg gcgggcatgc ctgttcgagc gtcatt                                 156

<210> SEQ ID NO 2
<211> LENGTH: 561
<212> TYPE: DNA
<213> ORGANISM: Paecilomyces tenuipes

<400> SEQUENCE: 2
aaaccaacag ggattgcccc agtaacggcg agtgaagcgg caacagctca aatttgaaat        60
ctggcccccg ggtccgagtt gtaatttgca gaggatgctt cgggcgaggt gccttccgag       120
ttccctggaa cgggacgcca cagagggtga gagccccgtc tggtcggaca ccgagcccgt       180
gtgaagctcc ttcgaagagt cgagtagttt gggaatgctg ctcaaaacgg gaggtatatg       240
tcttctaaag ctaaatattg gccagagacc gatagcgcac aagtagagtg atcgaaagat       300
gaaaagcact ttgaaaagag ggttaaaaag tacgtgaaat tgttgaaagg gaagcgccca       360
tgaccagact tgggcccggt gaatcacccg gcgttctcgc cggtgcactt tgccgggcac       420
aggccagcat cagtttggcg cggggagaa aggcttcggg aacgtggctc cctcgggagt       480
gttatagccc gctgcgcaat accctgcgcc ggactgaggt acgcgcatcg caaggatgct       540
ggcgtaatgg tcatcagcga c                                                 561
```